US 6,306,080 B1

(12) United States Patent
Mitchell et al.

(10) Patent No.: US 6,306,080 B1
(45) Date of Patent: Oct. 23, 2001

(54) DISPOSABLE PENILE CONSTRICTION DEVICE HAVING PREFORMED TEAR CONFIGURATION AND ASSOCIATED METHODS

(75) Inventors: John Mitchell, Appling; Phillip Jack Snoke; Chris Hamilton, both of Atlanta, all of GA (US)

(73) Assignee: Soma Blue, Inc., Augusta, GA (US)

( * ) Notice: Subject to any disclaimer, the term of this patent is extended or adjusted under 35 U.S.C. 154(b) by 0 days.

(21) Appl. No.: 09/401,430

(22) Filed: Sep. 22, 1999

(51) Int. Cl.[7] .................................................. A61F 5/00
(52) U.S. Cl. ............................................................ 600/38
(58) Field of Search ......................... 600/38–41; 606/141

(56) References Cited

U.S. PATENT DOCUMENTS

| | | | |
|---|---|---|---|
| D. 339,418 | 9/1993 | Flynn ................................. D24/143 |
| 1,221,518 | 4/1917 | Dygert . | |
| 1,383,944 | 7/1921 | Hart . | |
| 2,581,114 | 1/1952 | Larson . | |
| 3,461,863 | * 8/1969 | Sullinger ................................ 600/41 |
| 3,794,020 | 2/1974 | Bagby .................................... 128/79 |
| 4,139,007 | 2/1979 | Diamond ............................. 128/138 |
| 4,203,432 | 5/1980 | Koch ...................................... 128/79 |
| 4,394,918 | * 7/1983 | Grussen .............................. 215/243 |
| 4,564,006 | 1/1986 | Pomeranz ............................. 128/79 |
| 4,784,655 | 11/1988 | Campion et al. .................... 604/349 |
| 5,027,800 | 7/1991 | Rowland ................................ 128/79 |
| 5,085,209 | * 2/1992 | Gottschalk ............................ 600/41 |
| 5,178,266 | * 1/1993 | Villa ..................................... 206/150 |
| 5,190,178 | * 3/1993 | Luch .................................... 215/256 |
| 5,192,271 | 3/1993 | Kalb et al. ........................... 604/116 |
| 5,193,673 | * 3/1993 | Rathbone et al. .................. 206/150 |
| 5,221,251 | 6/1993 | Edminster ............................. 600/41 |
| 5,306,227 | 4/1994 | Osbon et al. ......................... 600/41 |
| 5,327,910 | 7/1994 | Flynn .................................. 128/842 |
| 5,336,157 | 8/1994 | Hale ...................................... 600/41 |
| 5,487,464 | * 1/1996 | Galbierz et al. ..................... 206/149 |
| 5,749,201 | * 5/1998 | Cochrane ............................... 53/281 |
| 5,775,527 | * 7/1998 | Bosl et al. ........................... 215/252 |
| 5,810,710 | 9/1998 | Burgos .................................. 600/41 |
| 5,860,911 | 1/1999 | Dolade Guardia ................... 600/39 |
| 5,873,813 | 2/1999 | Weiss .................................... 600/38 |
| 6,015,379 | * 1/2000 | Sachse .................................. 600/39 |

\* cited by examiner

*Primary Examiner*—John P. Lacyk
*Assistant Examiner*—Joseph A Cadugan
(74) *Attorney, Agent, or Firm*—Allen, Dyer, Dopplet, Milbrath & Gilchrist, P.A.

(57) ABSTRACT

A disposable penile constriction device and associated methods are provided. The disposable penile constriction device preferably includes a strip of bendable and stretchable material formed in a closed band shape when in a closed position so that inner surface peripheries of the strip of material substantially surround and abuttingly contact outer surface peripheries of a proximal portion of a penis when positioned thereon and a preformed predetermined tear region formed in the strip of material which readily allows tearing of the strip of material by the hand of a user so that the closed band shape is separated to an open position and the strip of material can be readily removed from a proximal portion of a penis without the necessity of moving the strip of material over a distal end of a penis. A method of using a penile constriction device is provided which preferably includes stretching a closed band of material, positioning the stretched closed band of material over a distal end and to a proximal portion of a penis of a user, releasing the stretch of the closed band of material so that inner surface peripheries of the closed band of material abuttingly contact outer surfaces of the proximal portion of the penis, and tearing the band of material in a preformed predetermined tear region thereof with the hand of the user.

48 Claims, 6 Drawing Sheets

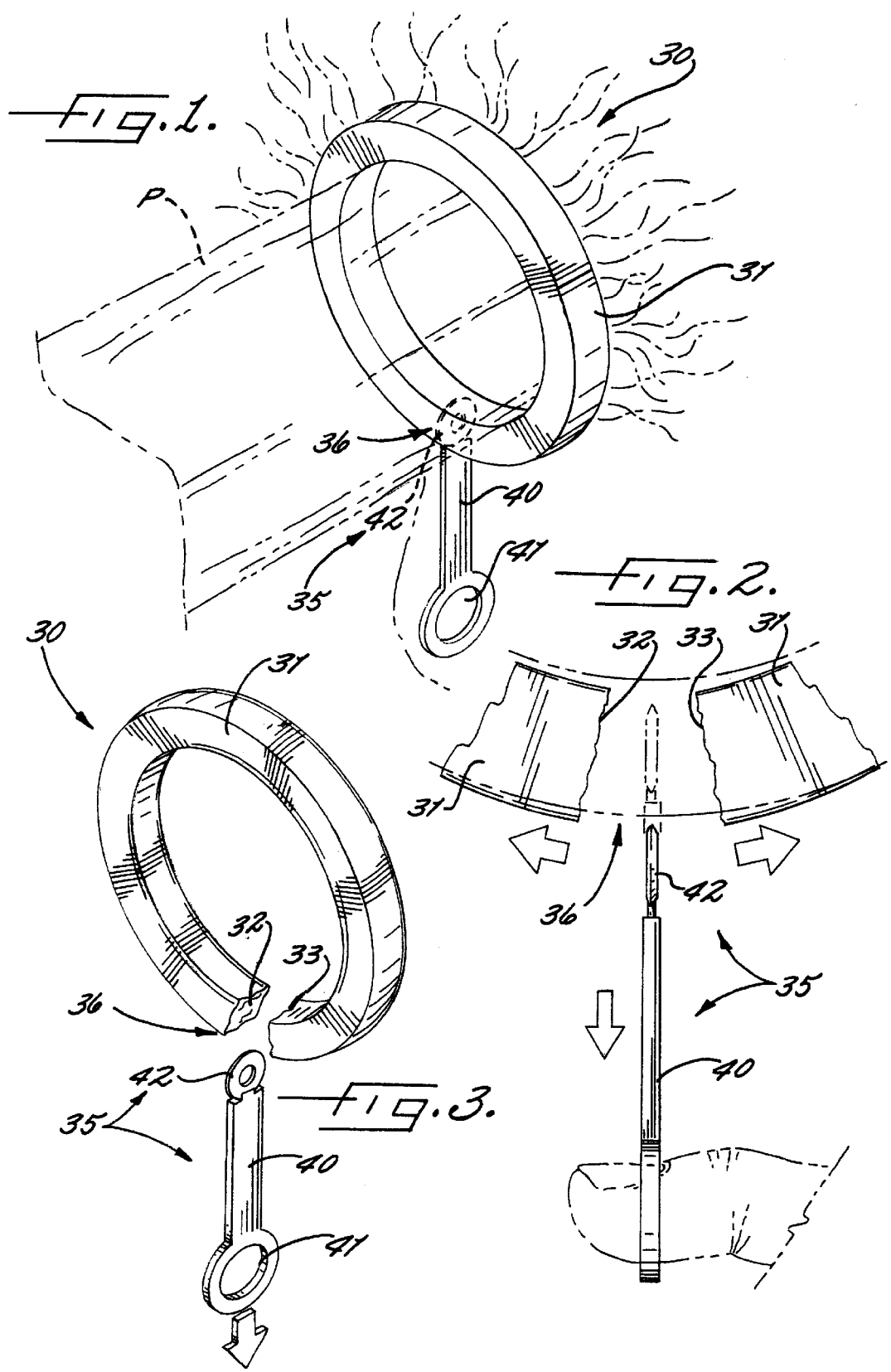

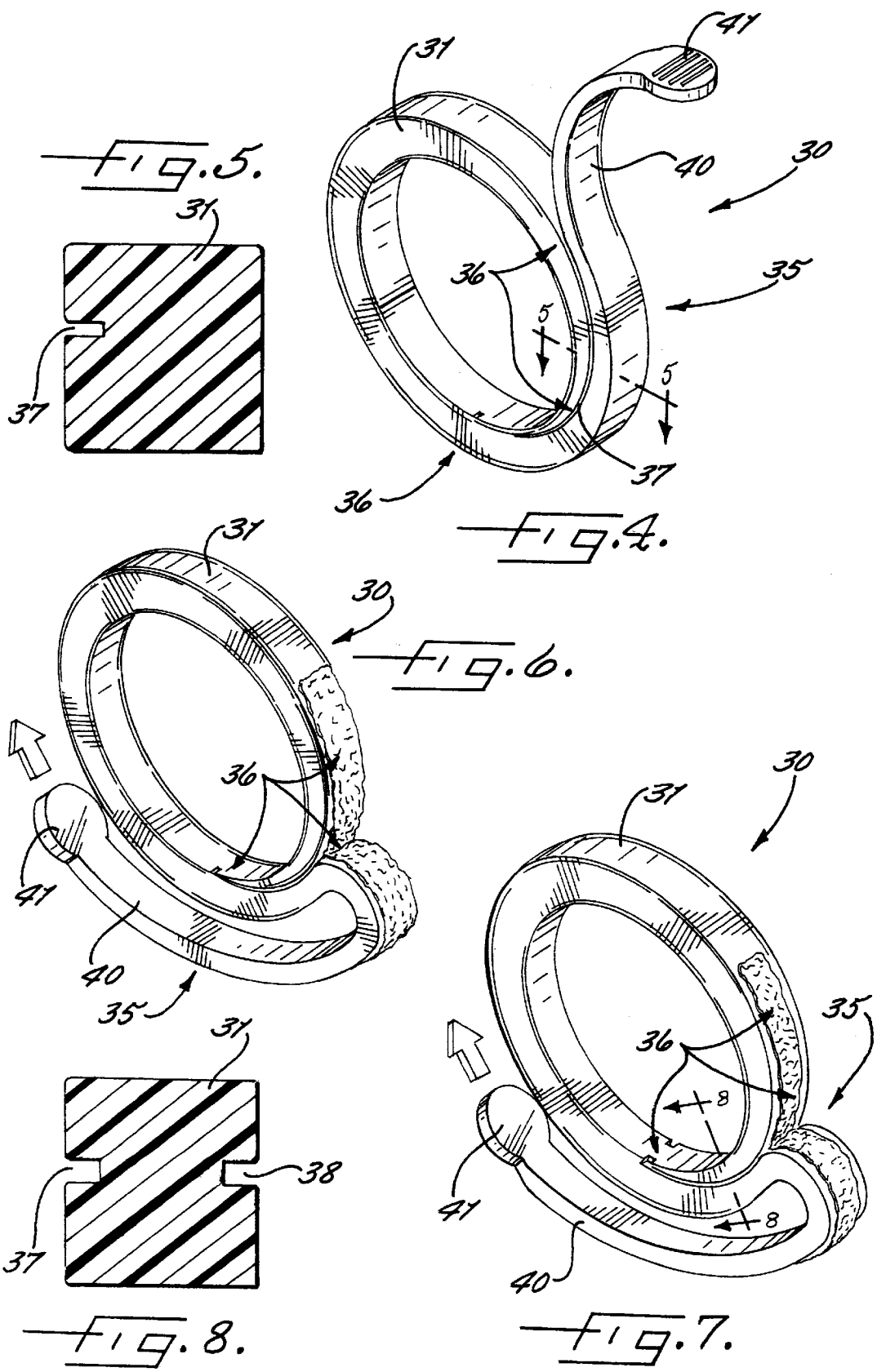

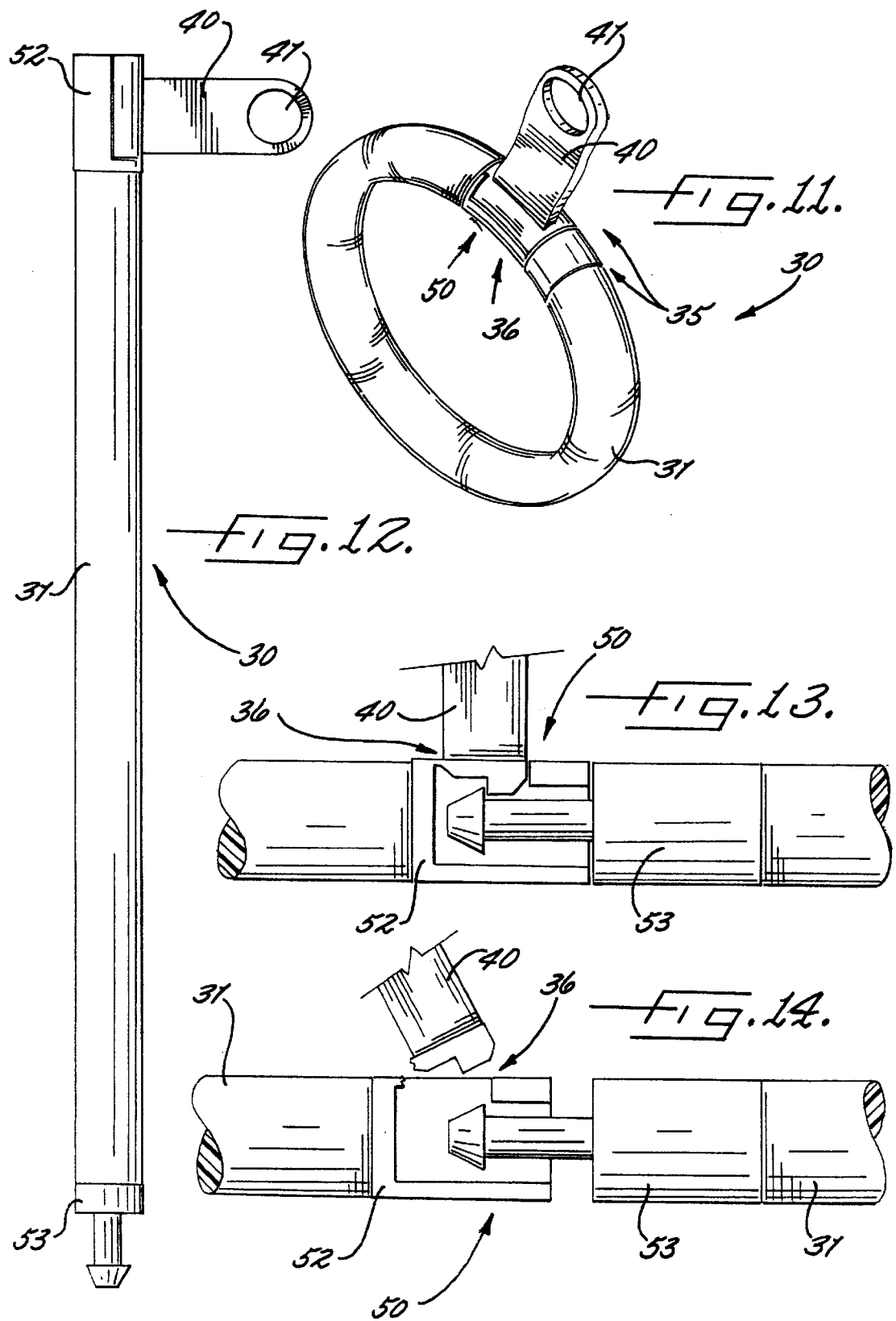

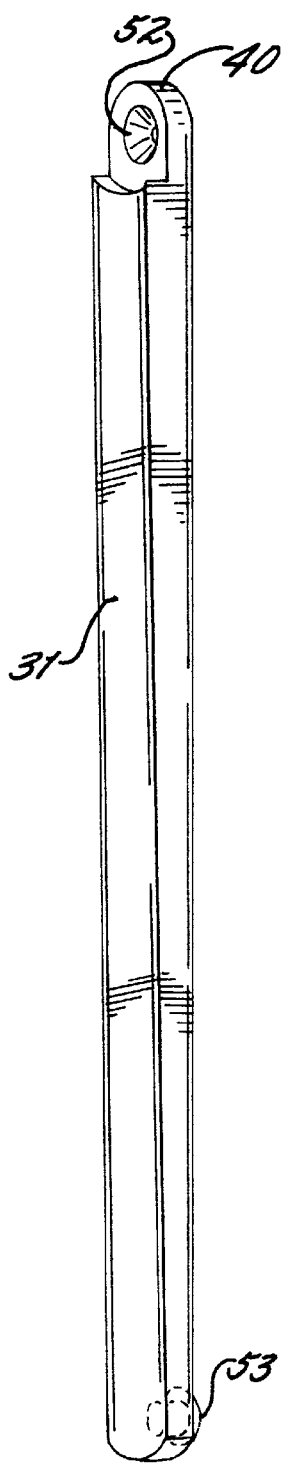
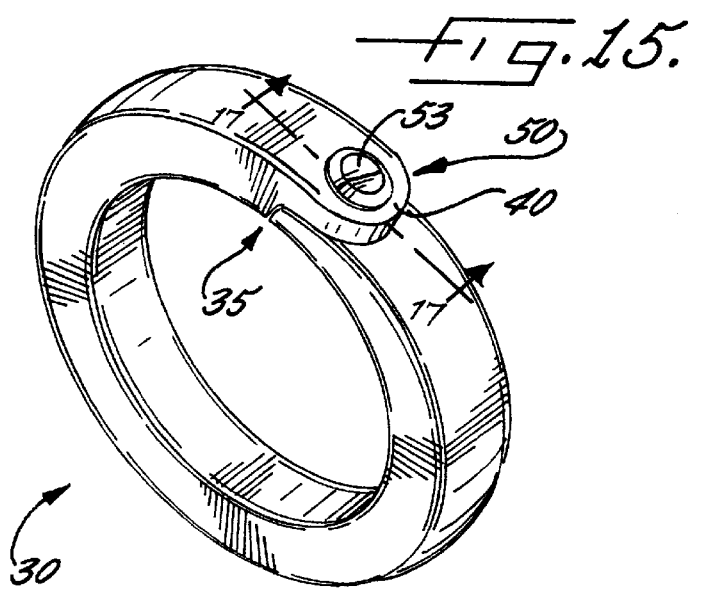
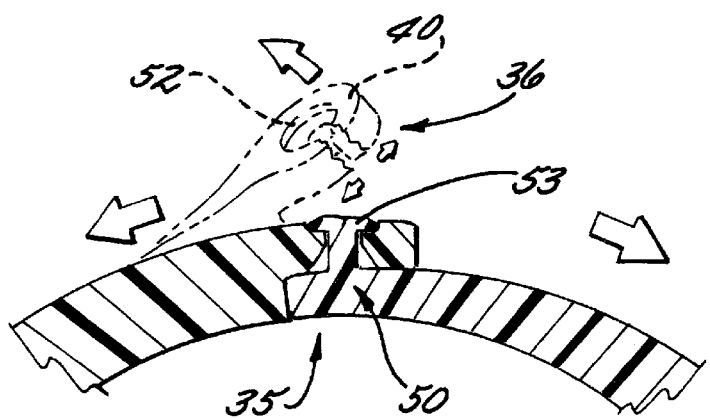

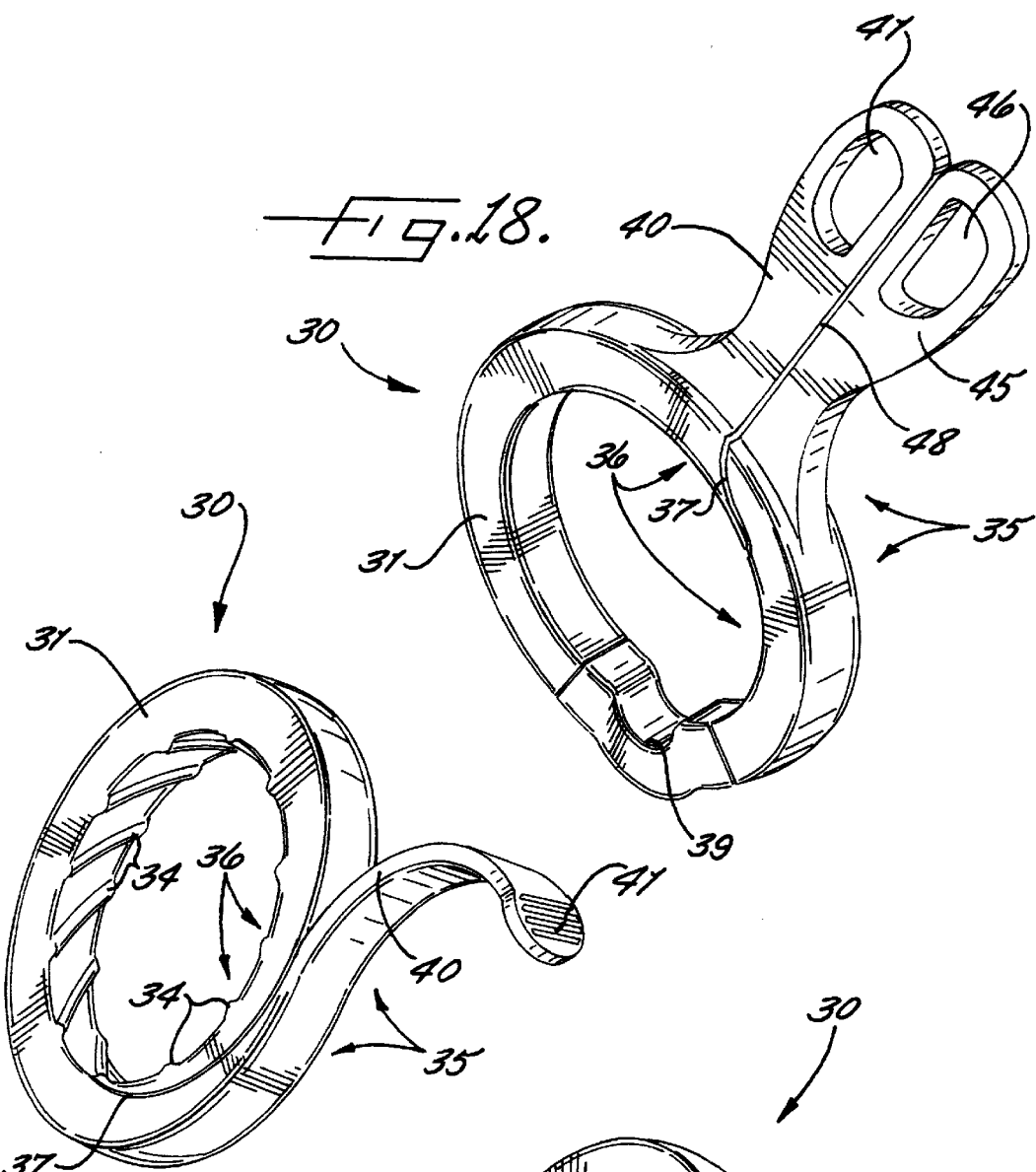
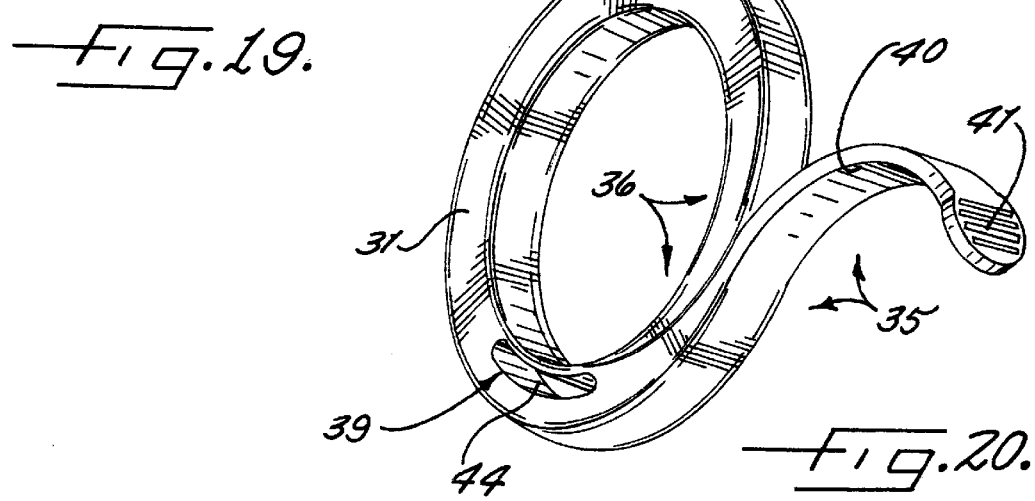

DISPOSABLE PENILE CONSTRICTION DEVICE HAVING PREFORMED TEAR CONFIGURATION AND ASSOCIATED METHODS

FIELD OF THE INVENTION

The present invention relates to the medical therapeutic industry and, more particularly, to the field of treatments for male impotence.

BACKGROUND OF THE INVENTION

Generally, in the male penis, an erection is produced when arterial blood flows to the erectile tissues of the penis, but the veinal return flow of blood to the body is restricted so that the erectile tissues become filled or engorged with blood. The restriction is normally performed by sphincter muscles which function in response to sexual arousal. Some men have various problems, e.g., advancing age, physiological or psychological problems, or premature relaxation prior to completion of coitus, with these sphincter muscles properly functioning. This often leaves these men unsatisfied with the sex act process.

By the recognition that penile arteries are located primarily in the deep interior of the male penis, and the return veins are located in a sub-dermal region along the surface of the organ, it has been known to secure a band of material around the base of the penis closely adjacent a user's body to restrict the return veinal blood flow. This assists in maintaining an erection while the arterial flow remains substantially unimpeded, i.e., the arteries are deep within the organ and protected from pressure by the erectile tissue.

Over the years, various types and configurations of bands for assisting in this restriction of the return veinal blood flow have been developed. Examples of such devices can be seen in U.S. Pat. No. 4,203,432 by Koch titled "Male Therapeutic Device," U.S. Pat. No. 5,027,800 by Rowland titled "Man's Erection Truss," U.S. Pat. No. 5,221,251 by Edminster titled "Penile Erection Sustainer," U.S. Pat. No. 5,306,227 by Osbon et al. titled "Apparatus For Augmenting Male Potency," and U.S. Pat. No. 5,810,710 by Burgos titled "Disposable Penile Adjustable Constriction Device." Some of these bands have been developed with a readily detachable fastener which allows the band to be positioned from a substantially open-band configuration to encircle the penis and fasten to a closed configuration. This type of band, however, can often be readily detached by loosening the fastener and is not capable of being stretched much in the closed position without the band or fastener breaking or the fastener detaching. The lack of stretching capabilities makes the band difficult, if not impossible, to use with a ring or band loading device which assists in positioning the band over the distal end and onto a proximal portion of a penis. Additionally, these types of bands require two hands of a user to fasten during the arousal state and can be cumbersome or awkward to use during this state, especially if an erection assist device is used as well.

Other of these bands, do not provide a fastener, but allow the closed band to be stretched for positioning over a distal end of the penis and moved to the proximal end, i.e., the base, of the penis for release into a penile constricted position. As suggested above, band stretching and positioning tools, e.g., a ring loader, have also been developed to aid in the positioning process of these bands. A problem with these types of bands, however, is that once the user is finished with the band and the band is in a tight constricted position, the band can be difficult to remove back over the distal end of the penis, especially over an enlarged organ and over the head of the penis. Also, a band left on a penis in the tight constricted position can cause bruising or other problems with the penis.

SUMMARY OF THE INVENTION

With the foregoing in mind, the present invention advantageously provides a disposable penile constriction device which can be both easily stretched in a closed band position for inserting over a male penis and yet can be readily detached without having to take the band back over the enlarged organ and over the head of the penis. The present invention also advantageously provides a disposable penile constriction device and associated methods which allow the user to readily break or tear the band for ease of removal from the base of a penis. The present invention additionally advantageously provides a disposable penile constriction device which can readily e molded in large quantities and yet still have the above described advantages. The present invention further advantageously provides a disposable penile constriction device and associated methods which can easily be used with vacuum assist erection devices, band or ring loaders, and other penile erection devices from various manufacturers and yet still have the above described advantages.

More particularly, the present invention provides a disposable penile constriction device which preferably includes a strip of bendable and stretchable material formed in a closed band shape when in a closed position so that inner surface peripheries of the strip of material substantially surround and abuttingly contact outer surface peripheries of a proximal portion of a penis when positioned thereon and preformed tearing means formed in the strip of material for readily tearing the strip of material by a hand of a user so that the closed band shape is separated to an open position and the strip of material can be readily removed from a proximal portion of a penis without the necessity of moving the strip of material over a distal end of a penis.

The present invention also advantageously provides methods of using, forming, and disposing of a penile constriction device. A method of using a penile constriction device preferably includes stretching a closed band of material, positioning the closed band of material over a distal end and to a proximal portion of a penis of a user, releasing the stretch of the closed band of material so that inner surface peripheries of the closed band of material abuttingly contact outer surfaces of the proximal portion of the penis, and tearing the band of material in a preformed predetermined tear region thereof with the hand of the user.

A method of forming a penile constriction device is provided according to the present invention which preferably includes molding a strip of material so that the strip of material defines a band shape when in a closed position and molding a predetermined tear region in the strip of material.

A method of disposing of a penile constriction device is also provided according to the present invention which preferably includes tearing a closed band of material mounted to a proximal portion of a penis of a user in a preformed predetermined tear region with the hand of the user to thereby open the closed band of material, removing the open and torn band of material from the proximal portion of the penis of the user, and discarding the band of material. The method can also include pulling a tear strap connected to the band of material in the preformed predetermined tear region so that the step of tearing the closed band of material occurs responsive to the pulling of the tear strap.

By the use of the preformed tearing means, a penile constriction device can readily be torn open by a hand of a user when positioned on a penis and then discarded, e.g., disposable. In other words, it is anticipated that a user will only use a particular penile constriction device once for each erection assisted episode and then a new penile constriction device will then be used. The penile constriction devices can advantageously be molded and formed relatively inexpensively according to the present invention. Penile constriction devices, including the one of the present invention, often are used in conjunction with a lubricant. As such, the present invention recognizes that disposing of the device after use can be quite desirable. Otherwise, cleaning or sterilizing such a device can be difficult, if not impossible, without significant damage to the device itself. Because a penile constriction device can desirably be disposable, the present invention greatly enhances the process of mounting and removing such a device after use and yet takes advantage of the recognition that tearing or breaking of the device is of little consequence since it will not be used again.

BRIEF DESCRIPTION OF THE DRAWINGS

Some of the features, advantages, and benefits of the present invention have been stated above. Others, however, also will become apparent as the description proceeds when taken in conjunction with the accompanying drawings in which:

FIG. 1 is a perspective environmental view of a disposable penile constriction device having a preformed tear configuration positioned at the base or proximal end portion of a male penis according to a first embodiment of the present invention;

FIG. 2 is an enlarged fragmentary side elevational view of a disposable penile constriction device having a user pulling a tear strap having a pull ring connected thereto according to a first embodiment of the present invention;

FIG. 3 is an exploded perspective view of a disposable penile constriction device having a preformed tear configuration illustrating the torn ring ember and the separated tear strap according to a first embodiment of the present invention;

FIG. 4 is a perspective view of a disposable penile constriction device having a preformed tear configuration according to a second embodiment of the present invention;

FIG. 5 is a sectional view of a disposable penile constriction device taken along line 5—5 of FIG. 4 and illustrating a preformed tear line according to a second embodiment of the present invention;

FIG. 6 is a perspective view of a disposable penile constriction device being torn by the pulling of a tear strap according to a second embodiment of the present invention;

FIG. 7 is a perspective view of a disposable penile constriction device being torn by the pulling of a tear strap according to a third embodiment of the present invention;

FIG. 8 is a sectional view of a disposable penile constriction device taken along line 8—8 of FIG. 7 and illustrating a pair of preformed tear lines according to a third embodiment of the present invention;

FIG. 11 is a perspective view of a disposable penile constriction device having a preformed tear configuration and in a connected position according to fifth embodiment of the present invention;

FIG. 12 is a side elevational view of a disposable penile constriction device in a disconnected position according to a fifth embodiment of the present invention;

FIG. 13 is an enlarged fragmentary elevational view of a disposable penile constriction device illustrating the connecting of a one-way fastener according to a fifth embodiment of the present invention;

FIG. 14 is an enlarged fragmentary elevational view of a disposable penile constriction device illustrating the tearing of a one-way fastener by use of a tear strap connected thereto according to a fifth embodiment of the present invention;

FIG. 15 is a perspective view of a disposable penile constriction device having a preformed tear configuration and illustrating a connected position according to a sixth embodiment of the present invention;

FIG. 16 is a side elevational view of a disposable penile constriction device and illustrating a disconnected position according to a sixth embodiment of the present invention;

FIG. 17 is a fragmentary sectional view of a disposable penile constriction device taken along line 17—17 of FIG. 15 and illustrating the tearing of a one-way fastener according to a sixth embodiment of the present invention;

FIG. 18 is a perspective view of a disposable penile constriction device illustrating a urethra notch according to a seventh embodiment of the present invention;

FIG. 19 is a perspective view of a disposable penile constriction device illustrating a plurality of ridges formed on inner surface peripheries according to an eighth embodiment of the present invention; and FIG. 20 is a perspective view of a disposable penile constriction device also illustrating a urethra notch according to a ninth embodiment of the present invention.

DETAILED DESCRIPTION OF PREFERRED EMBODIMENTS

The present invention will now be described more fully hereinafter with reference to the accompanying drawings, in which preferred embodiments of the invention are shown. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Like numbers refer to like elements throughout, and various prime notations, if used, indicate similar elements in alternative embodiments.

Figure 9:
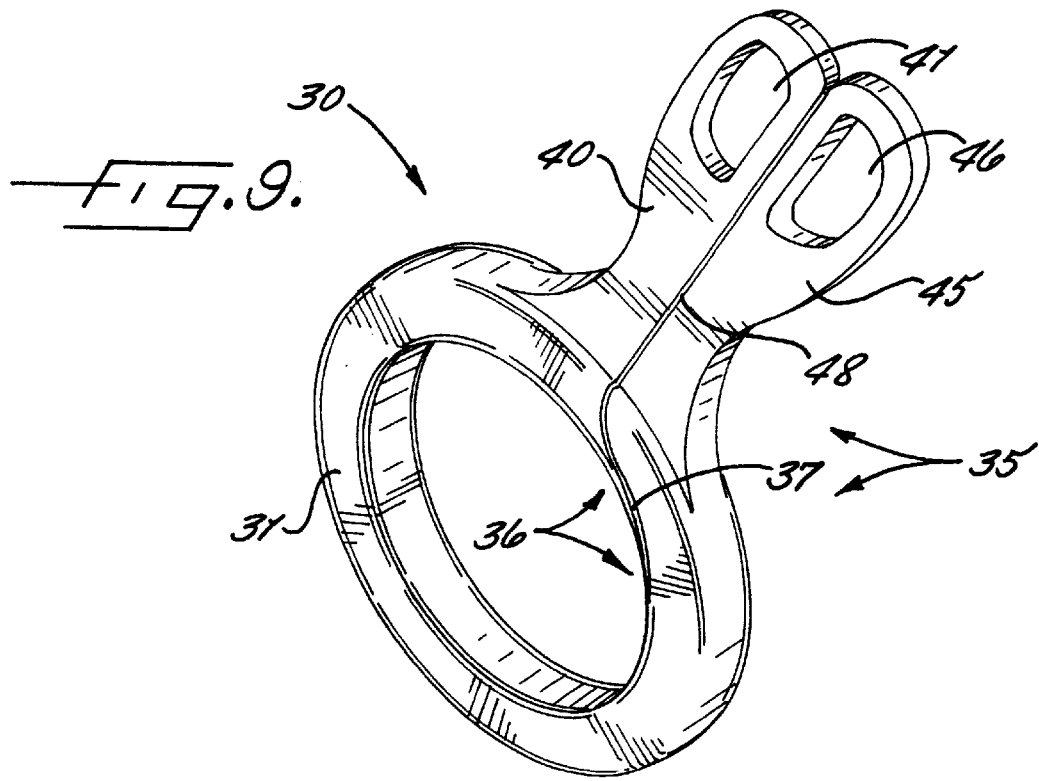
FIG. 9 is a perspective view of a disposable penile constriction device having a preformed tear configuration according to a fourth embodiment of the present invention.
Figure 10:
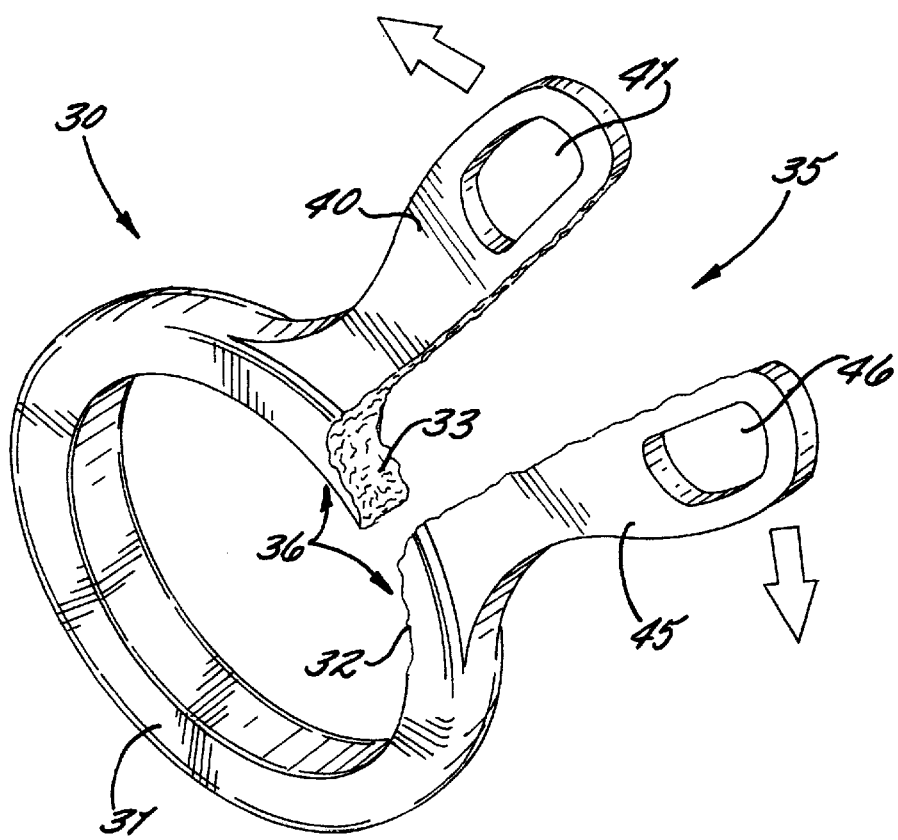
FIG. 10 is a perspective view of a disposable penile constriction device being separated or torn by a pair of tear straps according to a fourth embodiment of the present invention.

FIGS. 1–20 illustrate nine different embodiments of a disposable penile constriction device 30 according to the present invention. The penile constriction device 30 preferably includes a strip of bendable and stretchable material 31 formed in a closed band shape when in a closed position so that inner surface peripheries of the strip of material substantially surround and abuttingly contact outer surface peripheries of a proximal portion of a penis P (see FIG. 1) when positioned thereon and preformed tearing means 35 formed in the strip of material 31 for readily tearing the strip of material 31 by a hand of a user so that the closed band shape is separated to an open position (see FIGS. 2–3, 10, and 17) and the strip of material 31 can be readily removed from a proximal portion of a penis P without the necessity of moving the strip of material over a distal end of a penis.

As understood by those skilled in the art, the strip or band of material 31 can have a circular, rectangular or other polygonal, oval, or other shape in cross-section of the body thereof.

The strip of material 31 is preferably formed in a molding process, and the preformed tearing means 35 is also preferably formed in the strip of material 31 during the same molding process. The strip of material 31 is preferably formed of an elastomeric or other bendable and stretchable material, and preferably a material which is readily moldable, which allows extensive stretching of the band in a closed position for positioning on a penis P of a user and also for preferably using with an erection assist device, e.g., vacuum assist, as understood by those skilled in the art.

The preformed tearing means 35 preferably includes a predetermined tear region 36 of the strip of material 31. The strip of material 31 as illustrated preferably has a pair of non-predetermined tear end portions 32, 33, e.g., along the location of a tear or break, within the predetermined tear region 36 when in the open and torn position. The pair of non-predetermined end portions 32, 33 each have a roughened and uneven surface extending from outer surface peripheries to the inner surface peripheries of the strip of material 31 when in the open and torn position, i.e., so as to cause the separation of the band.

To assist the user in removal of the disposable penile constriction device 30, the predetermined tear region 36 preferably includes a tear strap 40 connected thereto so that a pulling force by a hand of a user of the tear strap 40 responsively causes the strip of material 31 in the predetermined tear region 36 to tear and thereby form the pair of non-predetermined end portions 32, 33. In a first embodiment, as illustrated in FIGS. 1–3, the tear strap 40 has a tear member 42 formed on an end thereof, surrounded by portions of the strip of material, and formed of a different hardness, e.g., semi-rigid, stiff, or harder elastomer, than the surrounding portions, e.g., over-molded softer material, so that the pulling force of the tear strap 40 by a user responsively causes the tear strap 40 and tear member 42 connected thereto to be separated from the strip of material 31. Pulling of the tear strap 40 causes the tear to propagate through the strip of material 31 when in the closed band configuration and result in the open position causing the band to fall off or be readily removed from the penis. The tear member 42 has a ring or circular shape as illustrated, but other shapes, e.g., diamond, rectangular, spherical, or other polygonal shapes, can be used as well according to the present invention.

In other embodiments, as illustrated in FIGS. 4–10, the predetermined tear region 36 preferably has portions of the strip of material 31 having an overlapping configuration. The tear strap 40 extends outwardly from the strip of material along the same radial direction as the strip of material 32, and the pulling force of the tear strap 40, e.g., in a direction preferably not to exceed about 120 degrees back from the natural extent of the molded tear strap, by a user responsively causes the strip of material 31 to unravel in the predetermined tear region 36. The tear strap 40 can likewise have a pull loop or opening formed therein as well according to these embodiments if desired. The overlapping configuration, for example, is illustrated by one end of the torn strip of material 31 overlying portions of the other end of the torn strip of material 31 when an attempt to reconstruct the closed band position is attempted.

Preferably, in these embodiments, the preformed tearing means 35 of the disposable penile constriction device 30 includes a portion of the strip of material 31 being thinner than other thicker surrounding portions. The thinner portion is preferably a channel or groove (see FIGS. 5 and 8) formed in the strip of material 31 and extending a predetermined distance. The channel or groove can be rectangular shaped in cross section as illustrated, but other V-shape, arcuate, or other shapes can be used as well according to the present invention. The thinner portion of the strip of material 31 preferably includes at least one preformed tear or score line 37, 38 (see FIGS. 4–8) defined by the extent of the channels or grooves formed in the molding process and extending from outer surface peripheries of the strip of material 31 when in the closed band shape position to the inner surface peripheries when in the closed band shape position. The at least one preformed tear or score line comprises a pair of preformed tear or score lines 37, 38 each positioned on opposite side peripheries of the strip of material 31 when in the closed band shape position. The tear strap 40 is preferably connected to the thinner portion of the strip of material 31 and is responsive to a pulling force by a user so that the strip of material 31 tears along at least the thinner portion thereof.

Alternatively, the preformed tearing means 35 can also include a portion of the strip of material 31 having a different hardness than other surrounding portions. The tear strap 40 is preferably connected to the portion having the different hardness than surrounding portions thereof and is responsive to a pulling force by a user so that the strip of material 31 tears along at least the portion having the different hardness. The preformed tearing means 35 preferably includes the predetermined tear region 36 of the strip of material 31 and at least one tear strap 40 connected to and extending outwardly from the predetermined tear region 36 of the strip of material 31 so that a pulling force of a user tears the strip of material 31 along the predetermined tear region 36.

Additionally, the tear strap 40 has at least one opening 41 formed therein so as to define a pull loop for gripping by a finger of a user and thereby enhance the tearing of the strip of material 31 to the open position. Instead of a pull loop 41, an enlarged tab region of the tear strap can be used as well for this purpose. As perhaps best illustrated in FIGS. 9–10 and 20, the at least one tear strap can include a pair of tear straps 40, 45 connected along a common tear line 48. Each of the pair of tear straps 40, 45 has the at least one pull loop 41, 46 connected thereto. Pulling of the at least a pair of pull loops 41, 46 by fingers of one or more hands of a user preferably readily separates the pair of tear straps 40, 45 along the common tear line 48 to thereby enhance the tearing of the strip of material 31 along one or more tear lines 37, 38 to the open position. This tearing or separating motion in this embodiment is a side to side tearing with two hands instead of the downward or outward motion of the other embodiments as illustrated. In this embodiment, the preformed tearing means 35 further includes a portion of the strip of material 31 likewise having one or more preformed tear lines 37, 38 extending from outer peripheries of the strip of material 31 when in the closed band shape position to inner peripheries when in the closed band shape position. The common tear or score line 48 of the pair of tear straps 40, 45 extends to and runs contiguous with the one or more preformed tear lines 37, 38 of the strip of material 31 (see also FIG. 20).

As perhaps best shown in FIGS. 11–17, the predetermined tear region 36 of the preformed tearing means 35 can also include a fastener 50 having portions 52, 53 thereof connected to end portions of the strip of material 31. The fastener 50 preferably readily closes but only opens by damage to the fastener 50 so that the fastener 50 cannot be readily used again and so as to define a one-way fastener whereby the strip of material 31 readily fastens in a closed band shape position and does not readily unfasten therefrom. The one-way fastener 50, for example, can have an opening as a female portion and a prong member as a male portion which snap-fit together prior to stretching for mounting on a penis. Also, these fastener configurations allow for other mounting techniques, but yet provide the advantages of a preformed tear configuration of the present invention. A pulling force by a user on a tear strap 40 which is also connected to the fastener 50 readily tears the one-way fastener 50 so that the strip of material 31 then readily extends to the open position.

Notably, in the embodiment of FIGS. 15–17, the tear strap 40 can be relatively short in length, but is preferably the longer lengths as illustrated in the other embodiments to enhance gripping by a user. This embodiment can also have the longer tear strap to extend outwardly away from the strip of material to form a loose end as compared to the tighter abuttingly contacting end of the tear strap as illustrated.

Likewise, in these embodiments, the strip of material 31 has a pair of non-predetermined tear end portions 32, 33 within the predetermined tear region 36 when in the open position. The non-predetermined tear end portions 32, 33, however, in these embodiments advantageously include at least portions of the one-way fastener 50. The pair of non-predetermined end portions 32, 33 each have a roughened and uneven surface extending from outer surface peripheries to the inner surface peripheries of the strip of material 31 when in the open position.

As perhaps best shown in FIGS. 18–20, further embodiments of a penile constriction device 30 preferably include the inner surface peripheries of the strip of material 31 having a plurality of pressure ridges 34 formed thereon which abuttingly contact a proximal portion of a penis P. These ridges 34 thereby provide a plurality of pressure contact regions around the outer surface peripheries of the proximal portion of a penis P. The strip of material 31 can also include a urethra notch 39 formed in the strip of material. The urethra notch 39 is preferably formed of a different hardness, e.g., softer, of the material or a different material altogether than surrounding portions thereof. For example, the urethra notch 39 can also be formed by portions of the material being absent or void 44 in a region of the material, e.g., an opening fully or partially extending through the strip of material 31, to be positioned closely adjacent a urethra of a penis (see FIG. 20) so that the region has a different harness than surrounding portions thereof.

As illustrated in FIGS. 1–20, the present invention also advantageously provides methods of using, forming, and disposing of a penile constriction device 30. A method of using a penile constriction device 30 preferably includes stretching a closed band of material 31, positioning the stretched closed band of material 31 over a distal end and to a proximal portion of a penis P of a user, releasing the stretch of the closed band of material 31 so that inner surface peripheries of the closed band of material 31 abuttingly contact outer surfaces of the proximal portion of the penis P, and tearing the band of material 31 in a preformed predetermined tear region 36 thereof with the hand of the user. The method can also include positioning a lubricant, e.g., an oil-based jelly or liquid, a water-based jelly or liquid, or various other lubricants as understood by those skilled in the art, on the band of material 31 prior to the step of positioning the stretched closed band of material 31 over a distal end of a penis P of a user.

A method of forming a penile constriction device 30 is provided according to the present invention which preferably includes molding a strip of material 31 so that the strip of material 31 defines a band shape when in a closed position and molding a predetermined tear region 36 in the strip of material 31.

A method of disposing of a penile constriction device 30 is also provided according to the present invention which preferably includes tearing a closed band of material 31 mounted to a proximal portion of a penis P of a user in a preformed predetermined tear region 36 with the hand of the user to thereby open the closed band of material 31, removing the open and torn band of material 31 from the proximal portion of the penis P of the user, and discarding the band of material 31. The method can also include pulling a tear strap 40 connected to the band of material 31 in the preformed predetermined tear region 36 so that the step of tearing the closed band of material 31 occurs responsive to the pulling of the tear strap 40.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A disposable penile constriction device comprising:
   a strip of bendable and stretchable material formed in a closed band shape when in a closed position so that inner surface peripheries of the strip of material is adapted to substantially surround and abuttingly contact outer surface peripheries of a proximal portion of a penis when positioned thereon; and
   preformed tearing means formed in the strip of material for readily tearing the strip of material by a hand of user so that the closed band shape is separated to an open position and the strip of material is adapted to be readily removed from a proximal portion of a penis without the necessity of moving the strip of material over a distal end of a penis when positioned thereon.

2. A device as defined in claim 1, wherein said strip of material is formed in a molding process, and wherein said preformed tearing means is formed in the strip of material during the same molding process.

3. A device as defined in claim 1, wherein said preformed tearing means includes a predetermined tear region of the strip of material, and wherein the strip of material has a pair of non-predetermined tear end portions within the predetermined tear region when in the open position.

4. A device as defined in claim 3, wherein the pair of non-predetermined end portions each have a roughened and uneven surface extending from outer surface peripheries to the inner surface peripheries of the strip of material when in the open position.

5. A device as defined in claim 4, wherein the predetermined tear region includes a tear strap connected thereto so that a pulling force by a user of the tear strap responsively causes the strip of material in the predetermined tear region to tear forming the pair of non-predetermined end portions.

6. A device as defined in claim 5, wherein the tear strap has a tear member formed on an end thereof, surrounded by portions of the strip of material, and formed of a different hardness than the surrounding portions so that the pulling force of the tear strap by a user responsively causes the tear strap and tear member to be separated from the strip of material.

7. A device as defined in claim 5, wherein the predetermined tear region has portions of the strip of material having an overlapping configuration, wherein the tear strap extends outwardly from the strip of material along the same radial direction as the strip of material, and wherein the pulling force of the tear strap by a user responsively causes the strip of material to unravel in the predetermined tear region.

8. A device as defined in claim 1, wherein said preformed tearing means includes a portion of the strip of material being thinner than other thicker surrounding portions.

9. A device as defined in claim 8, wherein the thinner portion includes at least one preformed tear line extending from outer surface peripheries of the strip of material when in the closed band shape position to the inner surface peripheries when in the closed band shape position.

10. A device as defined in claim 9, wherein the at least one preformed tear line comprises a pair of preformed tear lines each positioned on opposite side peripheries of the strip of material when in the closed band shape position.

11. A device as defined in claim 8, wherein said preformed tearing means further includes a tear strap connected to the thinner portion of the strip of material and being responsive to a pulling force by a user so that the strip of material tears along at least the thinner portion thereof.

12. A device as defined in claim 1, wherein said preformed tearing means includes a portion of the strip of material having a different hardness than other surrounding portions.

13. A device as defined in claim 12, wherein said preformed tearing means further includes a tear strap connected to the portion having the different hardness than surrounding portions thereof and being responsive to a pulling force by a user so that the strip of material tears along at least the portion having the different hardness.

14. A device as defined in claim 1, wherein said preformed tearing means includes a predetermined tear region of the strip of material and at least one tear strap connected to and extending outwardly from the predetermined tear region of the strip of material so that a pulling force of a user tears the strip of material along the predetermined tear region.

15. A device as defined in claim 14 wherein the at least one tear strap has at least one opening formed therein so as to define a pull loop for griping by a finger of a user and thereby enhance the tearing of the strip of material to the open position.

16. A device as defined in claim 15, wherein the at least one tear strap comprises a pair of tear straps connected along a common tear line, wherein each of the pair of tear straps has the at least one pull loop connected thereto, and wherein pulling of the respective each of the at least one pull loop of the pair of tear straps separates the pair of tear straps along the common tear line to thereby enhance the tearing of the strip of material to the open position.

17. A device as defined in claim 15, wherein said preformed tearing means further includes a portion of the strip of material having a preformed tear line extending from outer peripheries of the strip of material when in the closed band shape position to inner peripheries when in the closed band shape position, and wherein the common tear line of the pair of tear straps extends to and runs contiguous with preformed tear line of the strip of material.

18. A device as defined in claim 14, wherein the predetermined tear region of said preformed tearing means includes a fastener having portions thereof connected to end portions of the strip of material and which readily closes but only opens by damage to the fastener so as to define a one-way fastener whereby the strip of material readily fastens in a closed band shape position and does not readily unfasten therefrom, and wherein a pulling force by a user on said tear strap readily tears the one-way fastener so that the strip of material then readily extends to the open position.

19. A device as defined in claim 18, wherein the strip of material has a pair of non-predetermined tear end portions within the predetermined tear region when in the open position, the non-predetermined tear end portions including at least portions of the one-way fastener.

20. A device as defined in claim 19, wherein the pair of non-predetermined end portions each have a roughened and uneven surface extending from outer surface peripheries to the inner surface peripheries of the strip of material when in the open position.

21. A device as defined in claim 1, wherein the inner surface peripheries of the strip of material include a plurality of pressure ridges formed thereon which abuttingly contact a proximal portion of a penis to thereby provide a plurality of pressure contact regions around the outer surface peripheries of the proximal portion of a penis.

22. A device as defined in claim 1, wherein in the strip of material includes a urethra notch formed in the strip of material, the urethra notch being formed of a different hardness of the material than surrounding portions thereof.

23. A device as defined in claim 22, wherein the urethra notch is formed by portions of the material being absent in a region of the material to be positioned closely adjacent a urethra of a penis so that the region has a different harness than surrounding portions thereof.

24. A disposable penile constriction device comprising:
a strip of bendable and stretchable material formed in a closed band shape when in a closed position so that inner surface peripheries of the strip of material is adapted to substantially surround and abuttingly contact outer surface peripheries of a proximal portion of a penis when positioned thereon; and
a preformed predetermined tear region form in the strip of material which readily allows tearing of the strip of material by the hand of a user has been inserted between the words "user" and "so" so that the closed ban shape is separated to an open position and the strip of material is adapted to be readily removed from a proximal portion of a penis without the necessity of moving the strip of material over a distal end of a penis when positioned thereon.

25. A device as defined in claim 24, wherein said strip of material is formed in a molding process, and wherein said preformed predetermined tear region is formed in the strip of material during the same molding process.

26. A device as defined in claim 24, wherein the strip of material has a pair of non-predetermined tear end portions within the preformed predetermined tear region when in the open position.

27. A device as defined in claim 26, wherein the pair of non-predetermined end portions each have a roughened and uneven surface extending from outer surface peripheries to the inner surface peripheries of the strip of material when in the open position.

28. A device as defined in claim 27, wherein the preformed predetermined tear region further includes a tear strap connected thereto so that a pulling force by a user of the tear strap responsively causes the strip of material in the predetermined tear region to tear forming the pair of non-predetermined end portions.

29. A device as defined in claim 28, wherein the tear strap has a tear member formed on an end thereof, surrounded by portions of the strip of material, and formed of a different hardness than the surrounding portions so that the pulling force of the tear strap by a user responsively causes the tear strap and tear member to be separated from the strip of material.

30. A device as defined in claim 28, wherein the preformed predetermined tear region further has portions of the strip of material having an overlapping configuration, wherein the tear strap extends outwardly from the strip of material along the same radial direction as the strip of material, and wherein the pulling force of the tear strap by a user responsively causes the strip of material to unravel in the predetermined tear region.

31. A device as defined in claim 24, wherein the preformed predetermined tear region includes a portion of the strip of material being thinner than other thicker surrounding portions.

32. A device as defined in claim 31, wherein the thinner portion includes at least one preformed tear line extending from outer surface peripheries of the strip of material when in the closed band shape position to the inner surface peripheries when in the closed band shape position.

33. A device as defined in claim 32, wherein the at least one preformed tear line comprises a pair of preformed tear lines each positioned on opposite side peripheries of the strip of material when in the closed band shape position.

34. A device as defined in claim 31, wherein said preformed predetermined tear region further includes a tear strap connected to the thinner portion of the strip of material and being responsive to a pulling force by a user so that the strip of material tears along at least the thinner portion thereof.

35. A device as defined in claim 24, wherein said preformed predetermined tear region includes a portion of the strip of material having a different hardness than other surrounding portions.

36. A device as defined in claim 35, wherein said preformed predetermined tear region further includes a tear strap connected to the portion having the different hardness than surrounding portions thereof and being responsive to a pulling force by a user so that the strip of material tears along at least the portion having the different hardness.

37. A device as defined in claim 24, further comprising at least one tear strap connected to and extending outwardly from the strip of material so that a pulling force of a user tears the strip of material along the preformed predetermined tear region.

38. A device as defined in claim 37, wherein the predetermined tear region of said preformed tearing means includes a fastener having portions thereof connected to end portions of the strip of material and which readily closes but only opens by damage to the fastener so as to define a one-way fastener whereby the strip of material readily fastens in a closed band shape position and does not readily unfasten therefrom, and wherein a pulling force by a user on said tear strap readily tears the one-way fastener so that the strip of material then readily extends to the open position.

39. A device as defined in claim 38, wherein the strip of material has a pair of non-predetermined tear end portions within the predetermined tear region when in the open position, the non-predetermined tear end portions including at least portions of the one-way fastener.

40. A device as defined in claim 39, wherein the pair of non-predetermined end portions each have a roughened and uneven surface extending from outer surface peripheries to the inner surface peripheries of the strip of material when in the open position.

41. A device as defined in claim 24, wherein the at least one tear strap has at least one opening formed therein so as to define a pull loop for gripping by a finger of a user and thereby enhance the tearing of the strip of material to open position.

42. A device as defined in claim 41, wherein the at least one tear strap comprises a pair of tear straps connected along a common tear line, wherein each of the pair of tear straps has the at least one pull loop connected thereto, and wherein pulling of the respective each of the at least one pull loop of the pair of tear straps separates the pair of tear straps along the common tear line to thereby enhance the tearing of the strip of material to the open position.

43. A device as defined in claim 41, wherein said preformed tearing means further includes a portion of the strip of material having a preformed tear line extending from outer peripheries of the strip of material when in the closed band shape position to inner peripheries when in the closed band shape position, and wherein the common tear line of the pair of tear straps extends to and runs contiguous with reformed tear line of the strip of material.

44. A device as defined in claim 24, wherein the inner surface peripheries of the strip of material include a plurality of pressure ridges formed thereon which abuttingly contact a proximal portion of a penis to thereby provide a plurality of pressure contact regions around the outer surface peripheries of the proximal portion of a penis.

45. A device as defined in claim 24, wherein in the strip of material includes a urethra notch formed in the strip of material, the urethra notch being formed of a different hardness of the material than surrounding portions thereof.

46. A device as defined in claim 45, wherein the urethra notch is formed by portions of the material being absent in a region of the adapted material to be positioned closely adjacent a urethra of a penis so that the region has a different hardness than surrounding portions thereof.

47. A method of using a penile constriction device, the method comprising the steps of:

stretching a closed band of material;

positioning the stretched closed band of material over a distal end and to a proximal portion of a penis of user;

releasing the stretch of the closed band of material so that inner surface peripheries of the closed band of material abuttingly contact outer surfaces of the proximal portion of the penis;

tearing the band of material in a preformed predetermined tear region thereof with the hand of the user to thereby open the closed band of material;

removing the open and torn band of material from the proximal portion of the penis of the user without the necessity of moving the strip of material over a distal end of the penis; and discarding the band of material.

48. A method as defined in claim 47, further comprising the step of pulling a tear strap connected to the band of material in the preformed predetermined tear region so that the step of tearing the closed band of material occurs responsive to the pulling of the tear strap.

* * * * *

UNITED STATES PATENT AND TRADEMARK OFFICE
CERTIFICATE OF CORRECTION

PATENT NO. : 6,306,080 B1
DATED : October 23, 2001
INVENTOR(S) : Mitchell et al.

It is certified that error appears in the above-identified patent and that said Letters Patent is hereby corrected as shown below:

Column 2,
Line 18, between "readily" and "molded", please delete "e" and insert -- be -- therefor.

Column 3,
Line 40, between "ring" and "and" please delete "ember" and insert -- member -- therefor.

Column 4,
Line 3, between "to" and "fifth", please insert -- a -- therefor.

Column 7,
Line 47, please delete "harness" and insert -- hardness -- therefor.

Column 9,
Line 42, please delete "griping" and insert -- gripping -- therefor.

Column 10,
Line 27, please delete "harness" and insert -- hardness -- therefor.
Line 36, please delete "form" and insert -- formed -- therefor.
Line 38, please delete "has been inserted".
Line 39, please delete "between the words user and so".
Line 40, please delete "ban" and insert -- band -- therefore.

UNITED STATES PATENT AND TRADEMARK OFFICE
CERTIFICATE OF CORRECTION

PATENT NO. : 6,306,080 B1
DATED : October 23, 2001
INVENTOR(S) : Mitchell et al.

It is certified that error appears in the above-identified patent and that said Letters Patent is hereby corrected as shown below:

Column 12,
Line 22, after "with", please insert -- the -- therefor.
Line 23, please delete "reformed" and insert -- preformed -- therefor.
Line 30, between "wherein" and "the", please delete "in".

Signed and Sealed this

Nineteenth Day of March, 2002

Attest:

JAMES E. ROGAN
*Director of the United States Patent and Trademark Office*

*Attesting Officer*